United States Patent [19]

Stewart et al.

[11] 4,401,575
[45] Aug. 30, 1983

[54] BS AND W IN CRUDE OIL STREAMS

[75] Inventors: Thomas L. Stewart, Houston; Florian C. Demny, Pasadena, both of Tex.

[73] Assignee: Shell Oil Company, Houston, Tex.

[21] Appl. No.: 291,598

[22] Filed: Aug. 10, 1981

[51] Int. Cl.³ .............................................. B01R 17/02
[52] U.S. Cl. .................................. 210/746; 210/786; 210/96.1; 73/61.1 R
[58] Field of Search ............... 210/636, 742, 746, 773, 210/774, 781, 96.1; 73/61 R, 61.1 R; 184/1 E, 184/5, 6.24, 81, 100

[56] References Cited
U.S. PATENT DOCUMENTS

| 3,186,513 | 6/1965 | Dunn et al. ........................ 184/6.24 |
| 3,546,926 | 12/1970 | Dunavent, Jr. et al. ............. 73/61.1 |
| 3,767,014 | 10/1973 | Drone .................................. 184/6.24 |
| 4,184,952 | 1/1980 | Stewart ............................... 210/781 |

Primary Examiner—John Adee

[57] ABSTRACT

An improvement is provided in a process for measuring BS&W in crude oil by centrifugal separation of dry oil from wet oil and comparison of the dielectric constants of the two, the improvement being the use of at least two seals separating a dry oil chamber from a wet oil chamber and means for flushing the space between the seals with dry oil.

10 Claims, 1 Drawing Figure

BS AND W IN CRUDE OIL STREAMS

BACKGROUND OF THE INVENTION

A device for measurement of basic sediment and water (BS&W) in a predominantly non-aqueous stream (e.g. pipeline crude oil), is disclosed in U.S. Pat. No. 4,184,952. This device is an improvement on capacitance type instruments of the art which are dependent upon the extent to which the intrinsic dielectric constant of the subject fluid varies with time. The gravity and physical composition of crude oil are two factors which determine its intrinsic dielectric constant. If one or both of these properties should vary, instruments measure the accompanying change in the dielectric constant as percent BS&W. This yields an inaccurate measurement of BS&W because instruments must be initially set to read zero BS&W as the intrinsic dielectric constant of the fluid. The capacitance type instruments of the prior art have no means for automatically correcting the zero BS&W setting to compensate for periodic variations in the oil properties mentioned. By comparison, the device of U.S. Pat. No. 4,184,952 provides for automatic compensation of BS&W measurements by producing a clean, dry sample of the line fluid for measurement of its intrinsic dielectric constant. In this way, the true BS&W content of the fluid is measured by finding the difference between the dielectric constants of the wet and dry streams.

Even though the improvement over the prior art represented by the invention of U.S. Pat. No. 4,184,952 is substantial, it now has been discovered that other improvements can be made which even further increase the efficiency and accuracy of this invention. Thus, it has been discovered that seals between the wet oil and dry oil chambers occasionally leak after extended usage. In view of the extreme sensitivity of this device, any leakage, however small, can measurably reduce the accuracy of readings. Accordingly, it is desirable to provide a means which substantially eliminates the possibility of any leakage from the wet oil chamber to the dry oil chamber.

SUMMARY OF THE INVENTION

Figure 1:
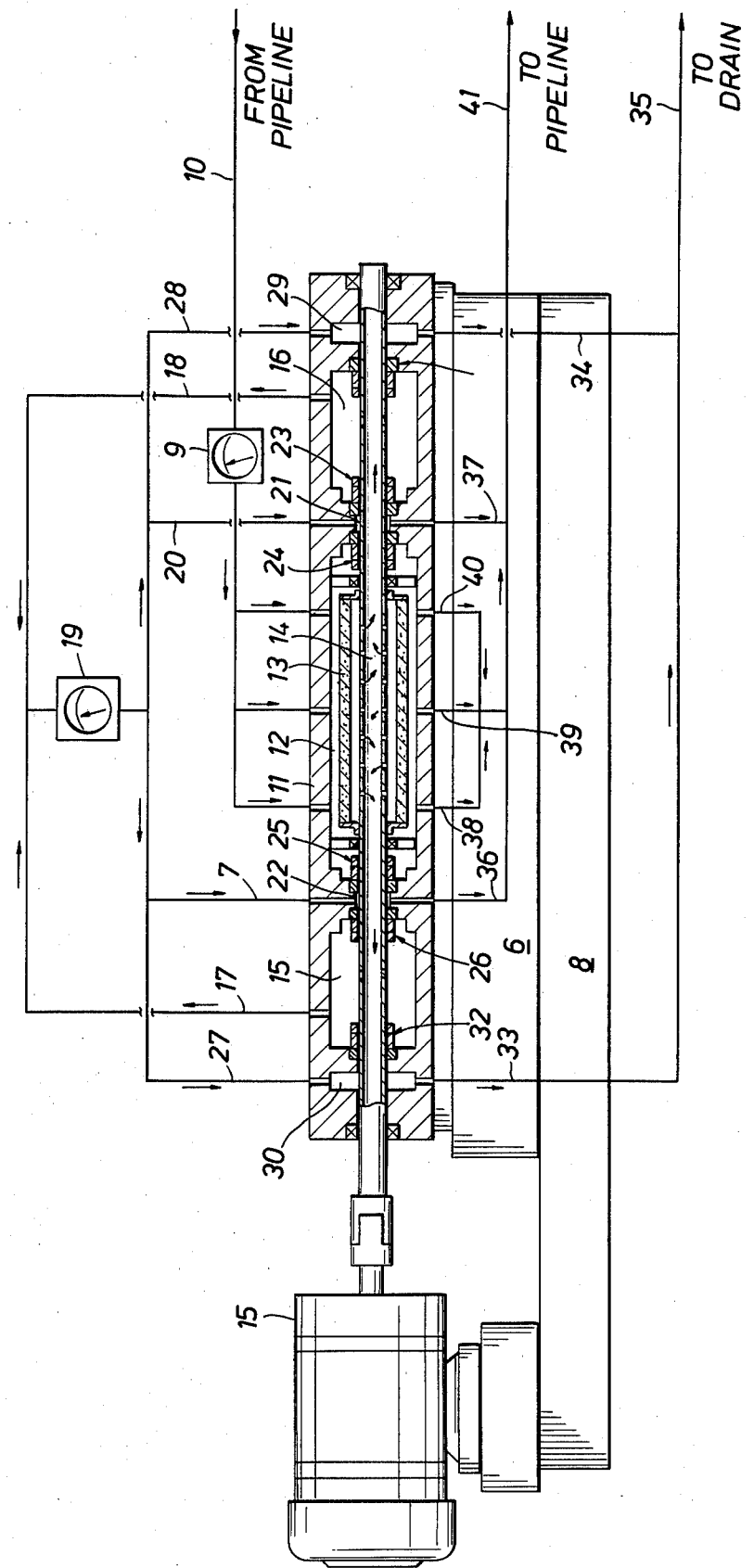
FIG. 1 schematically shows the flow paths of various streams within the apparatus of the invention.

The present invention pertains to a process and apparatus for flushing or cleaning between seals. More particularly, the process and apparatus utilize part of an internally produced dry fluid to clean or flush between seals separating the dry fluid from a wet fluid. Preferably, the dry fluid previously has been extracted from the wet fluid. In addition, the wet fluid may also contain sediment or other contaminants not present in the dry fluid.

Specifically, the present invention provides a process and apparatus for measuring the water and sediment content of a wet stream which is predominantly non-aqueous, by removing a sample of the wet stream, admitting the wet stream sample to an outer chamber containing an inner chamber having a wall formed of a filter, rotating the inner chamber while pressuring the wet stream sample from the outer chamber into the inner chamber, whereby sediment is filtered from the wet stream sample passing into the inner chamber and centrifugal force in the inner chamber forces water in the wet stream sample to remain or return to the outer chamber and thereby form a dry sample stream, passing the dry sample stream axially from the inner chamber to an aligned chamber which is separated from the outer chamber by at least two seals having a space therebetween, and passing a portion or all of the dry stream sample into the space between the seals. Preferably, the dry stream sample is subsequently returned to the pipeline. More preferably, the end of the aligned chamber opposite the end adjacent the outer chamber is provided with a seal, and a minor portion of the dry stream sample is passed into a space outside the aligned chamber which is adjacent the last said seal. Preferably, the minor portion of the dry stream sample subsequently is sent to disposal.

DESCRIPTION OF PREFERRED EMBODIMENTS

In accordance with the present invention, a process and apparatus are provided for incorporating the water-/oil emulsion separator in U.S. Pat. No. 4,184,952 into a complete system for determining basic sediment and water in crude oil, other hydrocarbons, or other substantially non-aqueous streams. This invention is particularly concerned with seals which separate a centrifugal filter such as shown in U.S. Pat. No. 4,184,952 from other chambers in the apparatus which enclose wet and dry streams. In accordance with the present invention, the dry stream is employed as a flush which (1) cools the seals, (2) prevents any wax or polymer buildup resulting from minute leakage and (3) reduces the loading on the seal faces by minimizing the differential pressure across the faces. Such a flush also is desirable on the extreme outboard seals which are at atmospheric pressure. A small amount of dry fluid drips over these seals and flows to drain.

A sectional view of the present invention is provided in FIG. 1 with flow streams shown schematically. Crude oil or other fluid containing a small amount of water is taken from a pipeline or other storage or transport via line 10 and passed through a wet oil capacitance measurement cell 9, and then through a housing 11 supported by structures 6 and 8, and then into wet oil chamber 12. Cell 9 determines the capacitance of the wet oil. From chamber 12, the wet oil is forced through filter 13 and into hollow drive shaft 14. Hollow drive shaft 14 and filter 13 are spun by a motor or other drive means 15. While the present invention is not limited to the following theory, it appears that the resulting centrifugal force substantially prevents the water and sediment capable of otherwise passing through filter 13, from entering hollow shaft 14, and any water or sediment that may enter shaft 14 is forced outwardly back into chamber 12. Dry fluid in hollow shaft 14 passes outwardly into dry oil chambers 15 and 16. Dry oil from chambers 15 and 16 then is passed via lines 17 and 18 through a dry oil capacitance measurement cell 19 which determines the capacitance of the dry oil. As above noted, comparison of the capacitance of the dry oil with the capacitance of the wet oil facilities determining the true BS&W content of the wet oil.

A portion of all of the dry oil stream 19 is passed via lines 7 and 20 into spaces 21 and 22 separating seals 23 and 24 and seals 25 and 26, respectively, which separate wet oil chamber 12 from dry oil chambers 15 and 16. An additional minor portion of the dry sample stream may be passed via lines 27 and 28 into spaces 29 and 30, which are adjacent outer seals 31 and 32 from the atmosphere. Spaces 29 and 30 are at atmospheric pressure, and accordingly, the dry oil therefrom is passed via lines 33, 34 and 35 to drain or disposal. Dry oil from spaces 21 and 22 is passed via lines 36 and 37 along with wet oil from lines 38, 39 and 40 back to the pipeline or other storage or transport via line 41.

While the present invention has been described principally in connection with a basic sediment and water instrument and in terms of crude oil and wet and dry streams of such crude oil, it will be apparent that the basic principles of the invention are adaptable to other processes and apparatus utilizing non-oil streams, where it is desirable to clean or flush seals between chambers containing different fluids.

What is claimed is:

1. A process for measuring the water and sediment content of a wet stream which is predominantly non-aqueous, comprising, removing a sample of the wet stream, admitting the wet stream sample to an outer chamber containing an inner chamber having a wall formed of a filter, rotation the inner chamber while pressuring the wet stream sample from the outer chamber into the inner chamber, whereby sediment is filtered from the wet stream sample passing into the inner chamber and centrifugal force in the inner chamber forces water in the wet stream sample to remain in the outer chamber and thereby form a dry sample stream, passing the dry sample stream axially from the inner chamber to an aligned chamber which is separated from the outer chamber by at least two seals having a space therebetween, and passing at least a portion of the dry stream sample into the space between the seals.

2. The process of claim 1 wherein capacitance of the dry stream sample is measured prior to passing the dry stream sample into the space between the seals.

3. The process of claim 1 wherein the end of the aligned chamber opposite the end adjacent the outer chamber is provided with a seal, and a minor portion of the dry stream sample is passed into a space outside the aligned chamber which is adjacent the last said seal.

4. The process of claim 3 wherein the minor portion of the dry stream sample subsequently is sent to disposal.

5. The process of claim 1 wherein the wet stream is pipeline crude oil.

6. An apparatus for measuring the water and sediment content of a wet stream which is predominantly non-aqueous, comprising, means for removing a sample of the wet stream, means for admitting the wet stream sample to an outer chamber containing an inner chamber having a wall formed of a filter, means for rotating the inner chamber while pressuring the wet stream sample from the outer chamber into the inner chamber to form a dry sample stream, means for passing the dry sample stream axially from the inner chamber to an aligned chamber which is separated from the outer chamber by at least two seals having a space therebetween, and means for passing at least a portion of the dry stream sample into the space between the seals.

7. The apparatus of claim 6 including means for measuring the capacitance of the dry stream sample which is located upstream of the means for passing the dry stream sample into the space between the seals.

8. The apparatus of claim 6 including a seal at the end of the aligned chamber which is opposite the end adjacent the outer chamber, and means for passing a minor portion of the dry stream sample into contact with that portion of the last said seal which is outside the aligned chamber.

9. The apparatus of claim 8 including means for subsequently sending the minor portion of the dry stream sample to disposal.

10. The apparatus of claim 9 wherein the wet stream is crude oil which is in a pipeline.

* * * * *